United States Patent
Chun et al.

(10) Patent No.: US 10,706,967 B2
(45) Date of Patent: Jul. 7, 2020

(54) APPARATUS AND SYSTEM FOR PROCESSING DIAGNOSTIC DATA ON THE BASIS OF MEDICAL INTERVIEW DATA AND CAMERA DATA

(71) Applicant: PARTNERS & CO Inc., Seongnam-si, Gyeonggi-do (KR)

(72) Inventors: Seichul Chun, Paju-si (KR); Wonjung Choe, Seoul (KR); Yeonseop Kim, Suwon-si (KR); Hyunho Kim, Seoul (KR); Haebeom Lee, Seoul (KR)

(73) Assignee: PARTNERS & CO Inc., Seongnam-si (KR)

( * ) Notice: Subject to any disclaimer, the term of this patent is extended or adjusted under 35 U.S.C. 154(b) by 261 days.

(21) Appl. No.: 15/493,140

(22) Filed: Apr. 21, 2017

(65) Prior Publication Data

US 2018/0260529 A1     Sep. 13, 2018

(30) Foreign Application Priority Data

Mar. 9, 2017 (KR) .................... 10-2017-0030051

(51) Int. Cl.
  *G16H 50/20*  (2018.01)
  *G16H 50/70*  (2018.01)
  *G16H 20/10*  (2018.01)

(52) U.S. Cl.
  CPC ............. *G16H 50/20* (2018.01); *G16H 20/10* (2018.01); *G16H 50/70* (2018.01)

(58) Field of Classification Search
  CPC .... G06F 19/00; G06F 19/3431; G06F 19/324; G06F 19/321; G16H 50/20; G16H 30/40;
  (Continued)

(56) References Cited

U.S. PATENT DOCUMENTS 5,935,060 A * 8/1999 Iliff ....................... G06F 19/325
                                                600/300
6,333,985 B1 * 12/2001 Ueda ................... A45D 44/005
                                                382/100
(Continued)

FOREIGN PATENT DOCUMENTS

JP    2007-004662 A        1/2007
KR    100596197 B1 *       7/2006
(Continued)

OTHER PUBLICATIONS

Gandlek et al., "Cross-Validation of Item Selection and Scoring for the SF-12 Health Survey in Nine Countries: Results from the IQOLA Project", Journal of Clinical Epidemiology vol. 51, Issue 11, Nov. 1998, pp. 1171-1178 (Year: 1998).*

(Continued)

*Primary Examiner* — Aryan E Weisenfeld
*Assistant Examiner* — Alaaeldin M Elshaer
(74) *Attorney, Agent, or Firm* — Park, Kim & Suh, LLC

(57) ABSTRACT

A diagnostic data processing apparatus based on medical interview data and camera data according to the present invention includes: an interview engine for transmitting information on a question about previously provided standardized items to a user terminal or a smart mirror; an analysis engine for receiving medical interview information including information on an answer corresponding to the information on the question from the user terminal or the smart mirror, determining a state of a user by analyzing the medical interview information, and diagnosing the state of the user by analyzing a picture or an image received from the user terminal or the smart mirror; and a proposal engine for proposing complementary and alternative medical contents corresponding to information on a result of the analysis to the user terminal or the smart mirror through the information (Continued)

on the result of the analysis performed by the analysis engine.

9 Claims, 20 Drawing Sheets

(58) Field of Classification Search
CPC .......... G16H 10/20; G06T 7/00; G06Q 30/02; G06Q 50/22
USPC .......................................... 705/2, 3; 351/178
See application file for complete search history.

(56) References Cited

U.S. PATENT DOCUMENTS

| | | | |
|---|---|---|---|
| 10,052,026 B1* | 8/2018 | Tran | G16H 50/30 |
| 2002/0035486 A1* | 3/2002 | Huyn | G06F 19/3418 |
| | | | 705/3 |
| 2002/0087364 A1* | 7/2002 | Lerner | G06Q 40/08 |
| | | | 705/4 |
| 2010/0066822 A1* | 3/2010 | Steinberg | G06K 9/00208 |
| | | | 348/77 |
| 2011/0007142 A1* | 1/2011 | Perez | G06T 13/80 |
| | | | 348/77 |
| 2011/0007174 A1* | 1/2011 | Bacivarov | G06K 9/00281 |
| | | | 348/222.1 |
| 2015/0055085 A1* | 2/2015 | Fonte | B29D 12/02 |
| | | | 351/178 |
| 2015/0074019 A1* | 3/2015 | Kosaka | G06Q 10/10 |
| | | | 706/12 |
| 2016/0328533 A1* | 11/2016 | Kawai | G16H 50/30 |
| 2017/0206691 A1* | 7/2017 | Harrises | G02B 27/0172 |
| 2017/0228517 A1* | 8/2017 | Saliman | G16H 10/20 |
| 2017/0372029 A1* | 12/2017 | Saliman | G16H 10/20 |
| 2018/0189457 A1* | 7/2018 | Plummer | G16H 50/70 |
| 2018/0253840 A1* | 9/2018 | Tran | G16H 50/30 |
| 2019/0117151 A1* | 4/2019 | Stern | G16H 10/60 |

FOREIGN PATENT DOCUMENTS

| | | |
|---|---|---|
| KR | 10-2009-0016211 A | 2/2009 |
| KR | 10-2017-0030977 A | 3/2017 |

OTHER PUBLICATIONS

Kyu-Jin Yoon et al. "Development and Validation of a Lao Juan Questionnaire", Chin J integr Med Jul. 2015:21 (7):500-506 (Year: 2015).*

Kyu-Jin Yoon et al., Development and Validation of a Lao Juan Questionnaire, Chin J integr Med Jul. 2015:21 (7):500-506.

Young-Jae Park et al., Development of a valid and reliable blood stasis questionnaire and its relationship to heart rate variability, Complementary Therapies in Medicine (2013) 21, 633-640.

Young-Jae Park et al., Development of a valid and reliable food retention questionnaire, European Journal of Integrative Medicine 5 (2013) 432-437.

Young-Jae Park et al., Development of a Valid and Reliable Phlegm Pattern Questionnaire, The Journal of Alternative and Complementary Medicine, vol. 17, No. 9, 2011, pp. 851-858.

Byoung-Hee Lee et al., Development of a valid and reliable seven emotions impairment questionnaire and assessment of its predictability for phlegm and blood stasis, Journal of Traditional Chinese Medicine, Aug. 15, 2016:36(4): 547-554.

Hyunhee Ryu et al., Reliability and Validity of a Cold-Heat Pattern Questionnaire for Traditional Chinese Medicine, The Journal of Alternative and Complementary Medicine, vol. 16, No. 6, 2010, pp. 663-667.

* cited by examiner

FIG. 4

| Groups | Subgroups | Items | Reference cut-off values |
|---|---|---|---|
| Seven emotions | 4 | 18 | 9 |
| Fatigue | 6 | 19 | 6 |
| Phlegm-retained fluid | 6 | 25 | 5 |
| Indigestion | 4 | 17 | 6 |
| Blood stasis | 3 | 12 | 3 |
|  | Total 23 | Total 91 |  |

FIG. 5

| Seven emotions | | |
|---|---|---|
| 18. Have amnesic symptoms | neuropsychology-related symptoms | |
| 13. Have conflicts among family members | | |
| 2. Feel pounding heartbeats | | |
| 4. Feel nervous at times | | |
| 6. Frequently startled all of sudden | | |
| 14. Feel worried and anxious at usual times | | |
| 17. Alternatingly feel cold and hot | psychosomatic symptoms | |
| 3. Feel a tightening chest | | |
| 7. Have a good appetite, but indigestive | | |
| 8. Feel dizzy | | |
| 5. Have chest pains | | |
| 10. Take a deep sigh | | |
| 1. Feel a pressure on the chest | | |
| 9. Feel tired at all times and desire only to lay down | depression-related symptoms | |
| 11. Feel subdued and life is uninteresting | | |
| 16. Sweat while sleeping | | |
| 15. Suffer from insomnia | sleep & emotion | |
| 12. Feel angry at times | | |

FIG. 6

| Fatigue | 1. Catch a cold frequently | common cold related symptoms |
|---|---|---|
| | 2. Cannot get over a cold for a long time | |
| | 3. If talk too much, get tired and voice fades away | |
| | 4. Do too much work more than physical strength | overworking related symptoms |
| | 5. Get much stress while working | |
| | 6. Irregular working times | |
| | 7. Decreased appetite | digestion-related symptoms |
| | 8. Indigestive | |
| | 9. Heavy arms and legs and hard to walk at usual times | |
| | 10. Hard to stand up or walk for a long time | |
| | 11. Completely exhausted if meals are skipped | fatigue-related |
| | 12. Drowsy and tired after meal | |
| | 13. Feel sick after work | |
| | 14. Always tired and drowsy | |
| | 15. Out of breath while working | etc |
| | 16. Frequently fevered | |
| | 17. Throat easily goes bad after talking | |
| | 18. Memory is failing day by day | |
| | 19. Suffer from or feel rectal prolapse | etc2 |

FIG. 7

| Phlegm-retained fluid | | |
|---|---|---|
| | 5. Feel fluttering in the chest | neuropsychology-related symptoms |
| | 6. Easily startled at trifles | |
| | 7. Feel a pressure on the chest | |
| | 24. Have joint pains in shoulders or knees | |
| | 11. Out of breath frequently | |
| | 4. Hear a sound from the ears | |
| | 25. Feel clamping pains in the sides | |
| | 16. Indigestive | digestion-related symptoms |
| | 17. Feel bloated with little food | |
| | 14. Decreased appetite | |
| | 15. Feel nauseous and vomiting at times | |
| | 18. Hear stomach growls | |
| | 2. Have headache at times | fatigue-related symptoms |
| | 1. Head does not feel clear | |
| | 12. Frequently feel tired | |
| | 3. Feel dizziness | |
| | 13. Does not have strength in arms and legs | |
| | 9. Get plenty of phlegm | respiration-related symptoms |
| | 10. Something is stuck in the throat and hard to spit or swallow | |
| | 8. Have cough | |
| | 22. Have shadows under eyes | skin-related symptoms |
| | 21. Face is somewhat yellowish | |
| | 20. Have soft lumps on the skin | etc |
| | 23. Itch skins | |
| | 19. Have somewhat loose or sticky stools | |

FIG. 8

| Indigestion | 1. Acid regurgitation into throat | digestion-related symptoms |
|---|---|---|
| | 2. Frequent belch | |
| | 3. Feel pains in stomach | |
| | 4. Have upset stomach | |
| | 5. Feel floated after meal | |
| | 6. Feel heartburn when pressed | |
| | 7. Feel body heavy | dampness-related symptoms |
| | 8. Weight gradually increases | |
| | 9. Easily swollen body | |
| | 10. More tired after meal | |
| | 11. Have stomach ache immediately after meal | food sensitivity-related symptoms |
| | 12. Pass stools immediately after meal | |
| | 13. Have stomach ache and traveler's diarrhea while traveling | |
| | 14. Get rashes with specific food | |
| | 15. Have somewhat loose stools at usual times | urine & feces-related symptoms |
| | 16. Frequently urinate | |
| | 17. Have joint pains in arms and legs | |

FIG. 9

| Blood stasis | | |
|---|---|---|
| | 1. Have pains in joints | pain-related symptoms |
| | 2. Hard to sleep at night with throbbing pains | |
| | 3. Feel pains in the sides | |
| | 4. Feel pains in lower abdomen | |
| | 5. Symptoms of numbed parts do not get well for a long time | |
| | 6. Get bruised easily | |
| | 7. Feel mass in abdomen | |
| | 8. Have blue or purple and dark shadows under eyes | blood vessel-related symptoms |
| | 9. Color of lip, tongue and gum is blue or purple and dark. | |
| | 10. Black stools | |
| | 11. Have symptoms of falling down or severely bumping like car accident | trauma-related symptoms |
| | 12. Have symptoms of sprained ankles, wrists or waist | |

APPARATUS AND SYSTEM FOR PROCESSING DIAGNOSTIC DATA ON THE BASIS OF MEDICAL INTERVIEW DATA AND CAMERA DATA

This application claims the benefit of Korean Patent Application No. 10-2017-0030051, filed on Mar. 9, 2017, the contents of which are hereby incorporated by reference herein in their entirety.

BACKGROUND OF THE INVENTION

Field of the Invention

The present invention relates to an apparatus and system for processing diagnostic data on the basis of medical interview data and camera data using Chinese medicine contents and an IoT terminal.

Background of the Related Art

Although it is easy to use various kinds of health information and disease information owing to advancement of the Internet, it is still difficult for general people to use the information since most of the information is oriented to medical experts, not to users.

Furthermore, in some cases, there is a problem in that although a patient feels sick, it is not easy to set up a measure and deal with the sickness if it is difficult to clearly identify a disease when the patient is medically diagnosed.

SUMMARY OF THE INVENTION

Therefore, an object of the present invention is to provide an apparatus and system for processing diagnostic data, which can improve health of an individual by processing the diagnostic data on the basis of medical interview data and camera data by utilizing complementary and alternative medicine.

A diagnostic data processing apparatus based on medical interview data and camera data according to an embodiment of the present invention may include: an interview engine for transmitting information on a question about previously provided standardized items to a user terminal or a smart mirror; an analysis engine for receiving medical interview information including information on an answer corresponding to the information on the question from the user terminal or the smart mirror, determining a state of a user by analyzing the medical interview information, and diagnosing the state of the user by analyzing a picture or an image received from the user terminal or the smart mirror; and a proposal engine for proposing complementary and alternative medical contents corresponding to information on a result of the analysis to the user terminal or the smart mirror through the information on the result of the analysis performed by the analysis engine.

The analysis engine may include: a medical interview determination engine for receiving the medical interview information including the information on the answer from the user terminal or the smart mirror and performing a diagnosis on the state of the user by analyzing the medical interview information; an ocular inspection determination engine for recognizing a face region from a picture or image data received from the user terminal or the smart mirror and performing a diagnosis on the state of the user through the face region; and a result determination engine for integrating diagnosis results of the medical interview determination engine and the ocular inspection determination engine and determining the state of the user using the results.

The medical interview determination engine may arbitrarily select an item from each subgroup of medical interview items divided into a predetermined number of groups, transmit a question about the items selected from the groups to the user terminal or the smart mirror in an arbitrary order, receive information on the answer to the question from the user terminal or the smart mirror, and determine a state of the user.

The medical interview determination engine may request an answer to the question in a point scale, calculate a score and a cut-off value of each group through the answer received in a point scale, and determine a state of the user by determining whether the cut-off value exceeds a reference cut-off value in each group.

If there is a group in which the state of the user is determined as mibyou as a result of arbitrarily selecting an item from each subgroup of the groups and transmitting a question about the items selected from the groups, the medical interview determination engine may question again all the items for the corresponding group, calculate again a score and a cut-off value of the corresponding group through an answer to the question received in a point scale, and finally determine a state of the user by determining whether a result calculated again exceeds a reference cut-off value of the corresponding group.

The ocular inspection determination engine may recognize a face region from the received data, extract major parts including eyes, a nose, a mouth, eyebrows and a chin, and perform a diagnosis on the state of the user using the recognized face region and the extracted major parts.

The ocular inspection determination engine may set a range of a numeric value of a specific color corresponding to a facial skin color to recognize the face region and set a region showing a numeric value recognized within the range as a face candidate region.

The major parts may correspond to feature points of the face region.

The ocular inspection determination engine may detect and formulate locations of the feature points and a ratio of distance between the feature points as an evaluation function and perform a diagnosis on the state of the user through information on the formulated evaluation function.

If there are two or more set face candidate regions, the ocular inspection determination engine may determine a face region of a largest label as a face region.

To extract eyes, which is a major part, the ocular inspection determination engine may examine whether a target object exists above and on the left side of a horizontal center line of the face region, examine whether a symmetrical object exists in a y coordinate symmetrical to a coordinate of the target object if the target object exists above and on the left side of a horizontal center line of the face region, and determine a symmetrical pair as eye regions if there is one symmetric pair as a result of the examination.

To extract a nose, which is a major part, the ocular inspection determination engine may examine whether a target object is located below and between the eye regions, examine whether a y coordinate distance of the target object from the eye regions is smaller than a reference value if the target object is located below and between the eye regions as a result of the examination, and determine the target object as the nose region if there is one target object as a result of the examination.

To extract a mouth, which is a major part, the ocular inspection determination engine may examine whether a target object exists below the nose region, examine whether the target object exists within outer boundaries of the coordinates of the two eyes if the target object exists below the nose region, and determine the target object as the mouth region if there is one target object as a result of the examination.

If feature points including the face region, the eye regions, the nose regions and the mouth regions are determined, the ocular inspection determination engine may analyze correlations between the feature points.

The ocular inspection determination engine may determine a correlation with a backbone through symmetry of a body, including symmetry of the feature points of the face region, angular symmetry of inclined shoulder lines, and symmetry of a pelvic region.

A diagnostic data processing system based on medical interview data and camera data according to an embodiment of the present invention may include: the diagnostic data processing apparatus described above; and a user terminal for transmitting information on an answer to the information on the question to the diagnostic data processing apparatus and transmitting a picture or an image photographed by a camera.

A diagnostic data processing system based on medical interview data and camera data according to an embodiment of the present invention may include: the diagnostic data processing apparatus described above; and a smart mirror for transmitting information on an answer to the information on the question to the diagnostic data processing apparatus and transmitting a picture or an image photographed by a camera.

The diagnostic data processing system may further include a provider terminal corresponding to a previously stored corresponding expert matching to information on a result of an analysis.

The diagnostic data processing apparatus may connect the expert of the provider terminal to a user of the user terminal or the smart mirror by providing the provider terminal with a result of a diagnosis according to the information on the result of the analysis.

The diagnostic data processing apparatus may transmit a result of a diagnosis according to the information on the result of the analysis to the user terminal or the smart mirror to output the analysis result.

BRIEF DESCRIPTION OF THE DRAWINGS

Detailed description of each drawing is provided to further sufficiently understand the drawings cited in the detailed description of the present invention.

FIG. 4 shows a table classifying medical interview items that the interview engine of FIG. 1 requests from a user.

FIGS. 5 to 9 respectively shows items in the groups of seven emotions, fatigue, phlegm-retained fluid, indigestion and blood stasis shown in FIG. 4.

DESCRIPTION OF SYMBOLS

Figure 1:
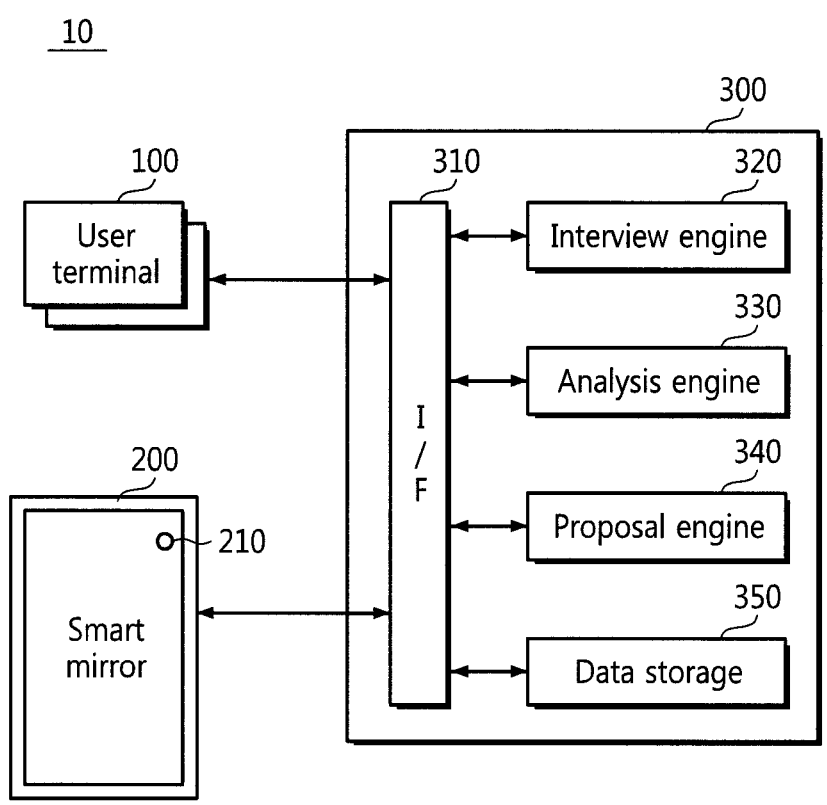
FIGS. 1 and 2 are views showing a diagnostic data processing apparatus based on medical interview data and camera data according to an embodiment of the present invention.

10: Diagnostic data processing system
100: User terminal
200: Smart mirror
300: Diagnostic data processing apparatus
310: Interface
320: Interview engine
330: Analysis engine
331: Medical interview determination engine
332: Ocular inspection determination engine
333: Result determination engine
340: Proposal engine
350: Data storage
400: Provider terminal

DETAILED DESCRIPTION OF THE PREFERRED EMBODIMENT

Figure 2:
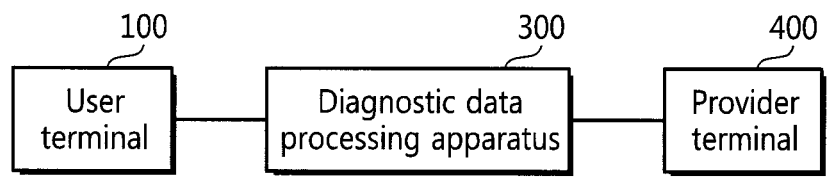

FIGS. 1 and 2 are views showing a diagnostic data processing system based on medical interview data and camera data according to an embodiment of the present invention. The diagnostic data processing system 10 includes a user terminal 100, a smart mirror 200 including a camera 210, and a diagnostic data processing apparatus 300.

The user terminal 100 may correspond to an IoT terminal including a portable device such as a smart phone, a tablet PC or the like and may transmit medical interview information input by a user of the user terminal 100 to the diagnostic data processing apparatus 300, and the camera 210 of the smart mirror 200 may transmit ocular inspection information including a picture or an image of the user of the user terminal 100 to the diagnostic data processing apparatus 300.

In this case, an application for transmitting and receiving data to and from the diagnostic data processing apparatus 300 may be installed in the user terminal 100.

The diagnostic data processing apparatus 300 includes an interface (I/F) 310, an interview engine 320, an analysis engine 330, a proposal engine 340 and a data storage 350.

The interface 310 receives medical interview information and ocular inspection information by performing data communication with the user terminal 100 and the smart mirror 200. In addition, the interface 310 transmits information on a result of analyzing the medical interview information and the ocular inspection information and related contents information to the user terminal 100 and the smart mirror 200.

The interview engine 320 may ask the user terminal 100 or the smart mirror 200 a question through previously provided standardized items. Specifically, the interview engine 320 may ask a question about ninety-one items and particularly may ask a question about representative twenty-three items among the ninety-one items. Details thereof will be described with reference to FIGS. 4 to 9.

The analysis engine 330 determines a state of the user, i.e., whether the user is in mibyou, by analyzing the medical interview information including information on an answer corresponding to the question received from the user terminal 100 or the smart mirror 200 and analyzes a picture or an image received from the user terminal 100 or the smart mirror 200, in which the analysis engine 330 detects a face region through the received picture or image and extracts and analyzes major parts including eyes, a nose and a mouth.

The analysis engine 330 will be described in detail with reference to FIG. 3.

The proposal engine 340 may propose or provide complementary and alternative medical contents corresponding to the information on the result of the analysis to the user terminal 100 or the smart mirror 200 through the information on the result of the analysis related to the medical interview and the ocular inspection performed by the diagnostic data processing apparatus 300.

The proposal engine 340 may recommend an expert registered in advance and corresponding to the information on the result of the analysis related to the medical interview and the ocular inspection performed by the analysis engine 330.

As shown in FIG. 2, the diagnostic data processing system 10 may further include a provider terminal 400.

The diagnostic data processing apparatus 300 may recommend a custom-tailored expert, who is a user of the provider terminal 400, using the medical interview information and the ocular inspection information received from the user terminal 100 and the smart mirror 200. To this end, the diagnostic data processing apparatus 300 may request and receive an advance registration from at least one provider terminal 400.

Figure 3:
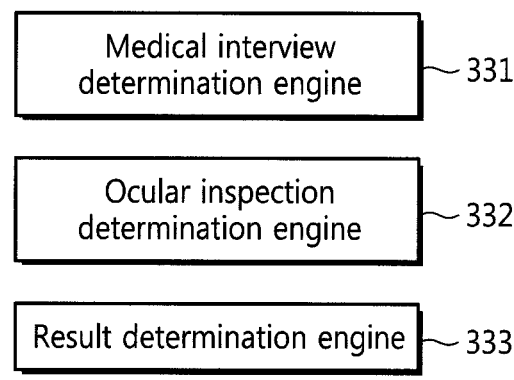
FIG. 3 is a block diagram showing the analysis engine 330 of FIG. 1.

FIG. 3 is a block diagram showing the analysis engine 330 of FIG. 1.

The analysis engine 330 includes a medical interview determination engine 331, an ocular inspection determination engine 332, and a result determination engine 333.

The medical interview determination engine 331 determines a state of the user, i.e., whether the user is in mibyou, by analyzing the medical interview information received from the user terminal 100 or the smart mirror 200. Here, although it is not a disease, the mibyou means a state of suffering from an inconvenience in a daily life due to physically, mentally or socially abnormal symptoms or showing abnormal findings when a medical examination is performed.

The medical interview determination engine 331 will be described below in more detail.

The ocular inspection determination engine 332 analyzes a picture or an image received from the user terminal 100 or the smart mirror 200, in which the ocular inspection determination engine 332 may perform a diagnosis by detecting a face region through the received picture or image and extracting and analyzing major parts including eyes, a nose and a mouth.

The ocular inspection determination engine 332 will be described below in more detail.

The result determination engine 333 integrates analysis results of the medical interview determination engine 331 and the ocular inspection determination engine 332, performs a diagnosis on the state of the user, and provides a diagnosis result to the user terminal 100 or the smart mirror 200.

FIG. 4 shows a table classifying medical interview items that the interview engine of FIG. 1 requests from a user. The items may be added, deleted or updated in the future.

The seven emotions are divided into four subgroups and have eighteen items, and its reference cut-off value is nine.

The fatigue is divided into six subgroups and has nineteen items, and its reference cut-off value is six.

The phlegm-retained fluid is divided into six subgroups and has twenty-five items, and its reference cut-off value is five.

The indigestion is divided into four subgroups and has seventeen items, and its reference cut-off value is six.

The blood stasis is divided into three subgroups and has twelve items, and its reference cut-off value is three.

FIGS. 5 to 9 respectively shows items in the groups of seven emotions, fatigue, phlegm-retained fluid, indigestion and blood stasis shown in FIG. 4. The items in the groups of seven emotions, fatigue, phlegm-retained fluid, indigestion and blood stasis are disclosed and described in detail in the Tables shown in FIGS. 5 to 9.

The basic items are as shown below.

A score and a cut-off value are separately calculated, and a degree of mibyou of each group is grasped from the calculated score.

Each item is scored in a five-point scale of "Strongly Disagree" (one point), "Disagree" (two points), "Neutral" (three points), "Agree" (four points) and "Strongly Agree" (five points).

After adding the result scored for each group, the added score is converted into a percentile score.

The user cannot see the cut-off value and may only confirm whether or not the user is in mibyou.

The reference cut-off value is a constant, which is a reference for determining whether or not the user is in mibyou.

The cut-off value is an on/off value scoring zero point in the case of "Strongly Disagree", "Disagree" or "Neutral" and scoring one point in the case of "Agree" or "Strongly Agree".

The cut-off value is calculated for each group, and it is examined whether or not the cut-off value exceeds the reference cut-off value.

If the cut-off value exceeds the reference cut-off value, it is determined as mibyou for the corresponding group.

<First Process>

Since it is probable that fatigue of a user will increase extremely if the user is questioned about all the ninety-one items, each group is subdivided into subgroups including sub-items having similar meanings, and one of the sub-items of a subgroup is arbitrarily selected as a representative item, and the user is questioned about the selected sub-item. In this case, the user may be simply questioned about representative twenty-three items among the ninety-one items.

The score is calculated by multiplying the number of items belonging to each subgroup as a weighting value.

Mibyou is determined by calculating a cut-off value and comparing the cut-off value with the reference cut-off value.

<Second Process>

In the case of the first process, since an arbitrary representative item of each subgroup is questioned and thus accuracy of determining mibyou may be relatively lowered, a solution as shown below is added.

For a group determined as mibyou through the first process, all the items of the corresponding group are questioned again, and an accurate score is calculated again, and in the same manner as described above, the cut-off value is calculated again, and whether or not the user is in mibyou is determined again by comparing the cut-off value with the reference cut-off value.

The present invention has an advantage of lowering fatigue of a user by reducing the number of first question items through the first and second processes and has an advantage of improving accuracy by questioning again about a group estimated as mibyou through the first process.

Hereinafter, a case of the first and second processes will be described.

<A Case>

First, the first question items are described only for the seven emotions.

Subgroups of the seven emotions are four as shown below.

A: neuropsychology-related symptoms (six items)
B: psychosomatic symptoms (five items)
C: depression-related symptoms (five items)
D: sleep & emotion (two items)

For example, points of items arbitrarily selected from each subgroup are as shown below.

A: 5 (Strongly Agree)
B: 2 (Disagree)
C: 4 (Agree)
D: 1 (Strongly Disagree)

A score of the seven emotions is calculated by multiplying a weighting value (the number of sub-items of a subgroup) as shown below.

$$6 \times 5 + 5 \times 2 + 5 \times 4 + 2 \times 1 = 62$$

A perfect score is obtained when all the items are "Strongly agree".

$$6 \times 5 + 5 \times 5 + 5 \times 5 + 2 \times 5 = 90$$

The percentile score is as shown below.

$$62/90 \times 100 = 68.89$$

Cut-off values of the subgroups are as shown below.
A: 1
B: 0
C: 1
D: 0

The cut-off value of the seven emotions is as shown below.

$$6 \times 1 + 5 \times 0 + 5 \times 1 + 2 \times 0 = 11$$

In the case of the seven emotions, since the reference cut-off value is 9 and value 11 exceeds the reference cut-off value, it is first determined that the seven emotions is in mibyou. That is, since 11>9, it is first determined as mibyou.

The second question is limited to the seven emotions.

All the items (eighteen items) are questioned again without considering the subgroups of the seven emotions.

It is assumed that points of the items are as shown below.
5, 4, 3, 2, 1, 5, 4, 3, 2, 1, 5, 4, 3, 2, 1, 5, 4, 3

A score of the seven emotions is calculated as shown below.

$$5+4+3+2+1+5+4+3+2+1+5+4+3+2+1+5+4+3=52$$

A perfect score is obtained when all the items are "Strongly agree".

$$18 \times 5 = 90$$

Then, the percentile score is as shown below.

$$52/90 \times 100 = 57.78$$

Cut-off values of the items are as shown below.
1, 1, 0, 0, 0, 1, 1, 0, 0, 0, 1, 1, 0, 0, 0, 1, 1, 0

The cut-off value of the seven emotions is as shown below.

$$1+1+1+1+1+1+1=6$$

In the case of the seven emotions, since the reference cut-off value is 9 and value 6 does not exceed the reference cut-off value, it is finally determined that the seven emotions is not in mibyou. That is, since 6<9, it is not in mibyou.

Figure 10:
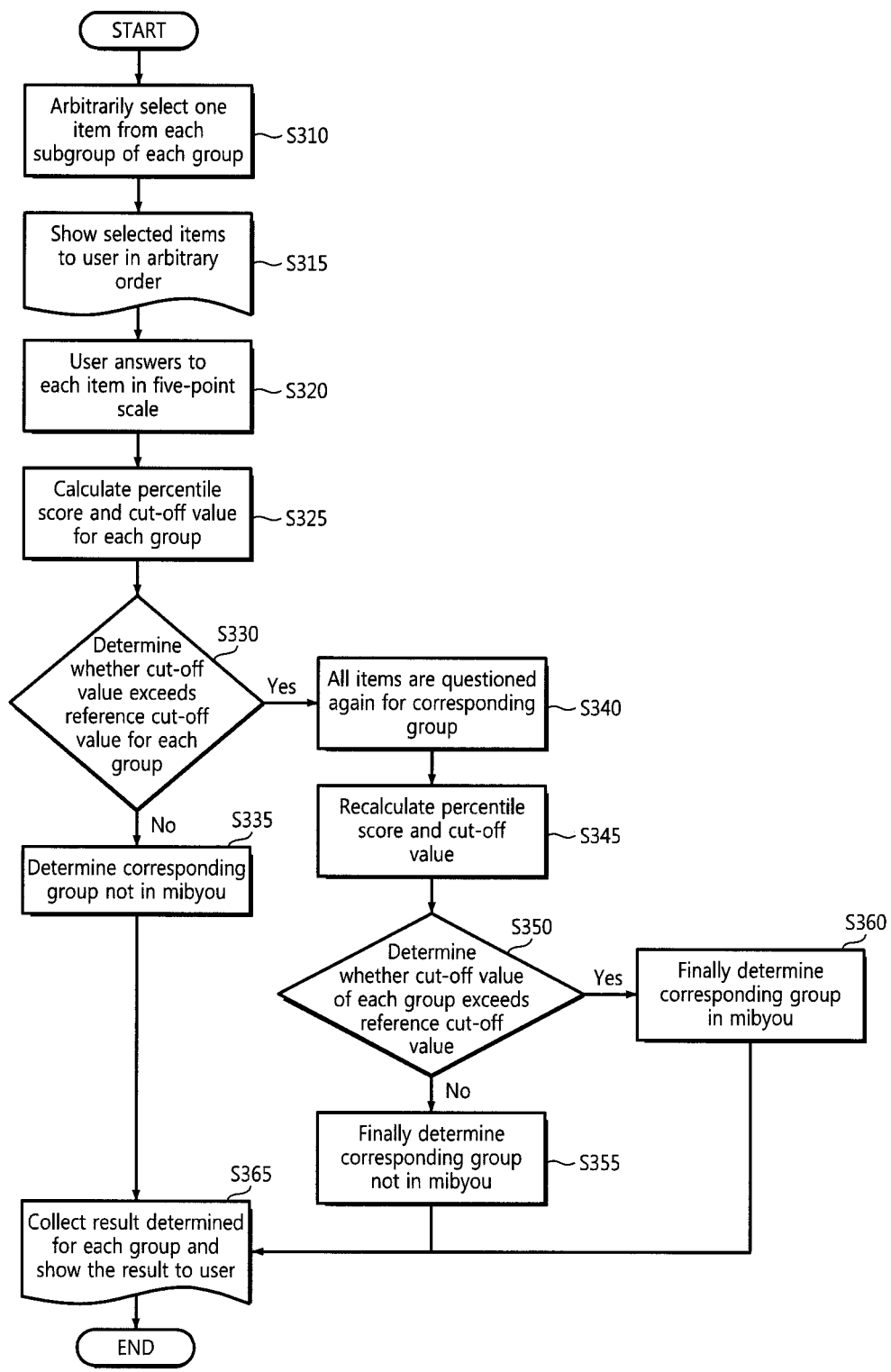
FIG. 10 is a general flowchart illustrating a method of medical interview according to an embodiment of the present invention.

FIG. 10 is a general flowchart illustrating a method of medical interview according to an embodiment of the present invention. The method of medical interview may be performed by the medical interview determination engine 331 of the diagnostic data processing system 10 of FIG. 1.

An item is arbitrarily selected from each subgroup of each group (step S310). The selected items are shown to a user in an arbitrary order (step S315).

The user answers to each item in a five-point scale (step S320).

A percentile score and a cut-off value are calculated for each group (step S325), and whether the cut-off value exceeds a reference cut-off value is determined for each group (step S330).

If it is determined otherwise at step S330 as a result of the determination, it is determined that the corresponding group is not in mibyou (step S335), and if the cut-off value exceeds the reference cut-off value as a result of the determination at step S330, all the items are questioned again for the corresponding group (step S340).

Thereafter, a percentile score and a cut-off value of each group are calculated again (step S345).

It is determined whether the cut-off value of each group exceeds a reference cut-off value (step S350). If the cut-off value exceeds the reference cut-off value as a result of the determination at step S350, it is finally determined that the corresponding group in mibyou (step S360), and if it is determined otherwise at step S350 as a result of the determination, it is finally determined that the corresponding group is not in mibyou (step S355).

Finally, the results determined for each of the groups are collected and output through the user terminal and shown to the user (step S365).

Figure 11:
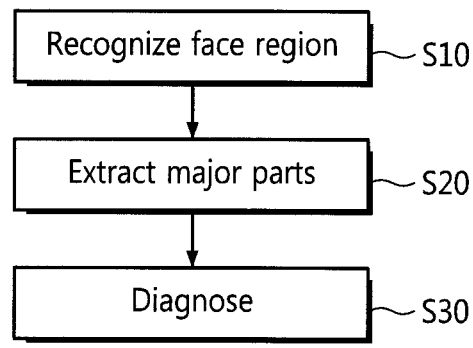
FIG. 11 is a general flowchart illustrating a method of ocular inspection according to an embodiment of the present invention.

FIG. 11 is a general flowchart illustrating a method of ocular inspection according to an embodiment of the present invention. The method of ocular inspection may be performed by the ocular inspection determination engine 332 of the diagnostic data processing system 10 of FIG. 1.

Referring to FIG. 11, a face region is recognized (step S10). A range of a numeric value of a specific color corresponding to a skin color is set to recognize a face region, and a region showing a numeric value recognized within the range may be set as a face candidate region.

An ellipsoidal mask operation may be additionally applied to the detected face candidate region, and efficiency of extracting the feature points, which will be described at step S20, can be enhanced through the ellipsoidal mask operation. For example, regions other than the face candidate region can be removed using an ellipsoidal mask, which is a mask of an ellipsoidal shape, on the detected face candidate region. A further correct face region can be recognized by removing the background and the neck portion having a color value similar to that of the face through the ellipsoidal mask.

Next, major parts including eyes, a nose, a mouth, eyebrows and a chin are extracted (step S20). The major parts may correspond to the feature points of the face region, and locations of the feature points and a ratio of distance between the feature points may be detected and formulated as an evaluation function.

Then, a diagnosis is performed through information on the formulated evaluation function (step S30). The information on the formulated evaluation function is classified to be matched to two or more of previously stored eye-type information, nose-type information, mouth-type information, eyebrow-type information and chin-type information by comparing the information on the formulated evaluation function with two or more of the previously stored eye-type information, nose-type information, mouth-type information, eyebrow-type information and chin-type information, and then the face is analyzed through the classified information, and a diagnosis is performed according to the analysis. Additional description on the diagnosis will be given after describing FIG. 13.

Figure 12:
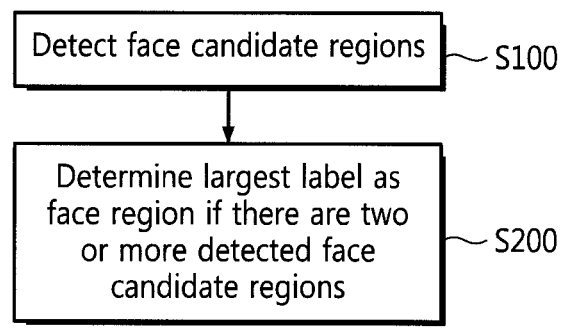
FIG. 12 is a flowchart for recognizing a face region in an ocular inspection method according to an embodiment of the present invention.

FIG. 12 is a flowchart for recognizing a face region in an ocular inspection method according to an embodiment of the present invention. The ocular inspection method may be performed by the ocular inspection determination engine 332 of the diagnostic data processing system 10 of FIG. 1.

The ocular inspection determination engine 332 detects a face candidate region as shown at S10 of FIG. 11 (step S100) and determines a face region of the largest label as a face region if there are two or more detected face candidate regions (step S200). For example, the ocular inspection determination engine 332 recognizes a region having a specific color value as a face candidate region and determines a face region of the largest label as a face region if there are two or more recognized face candidate regions, and the reason is that the face is the largest among the regions having a specific color value (e.g., a face, a hand and the like).

Figure 13:
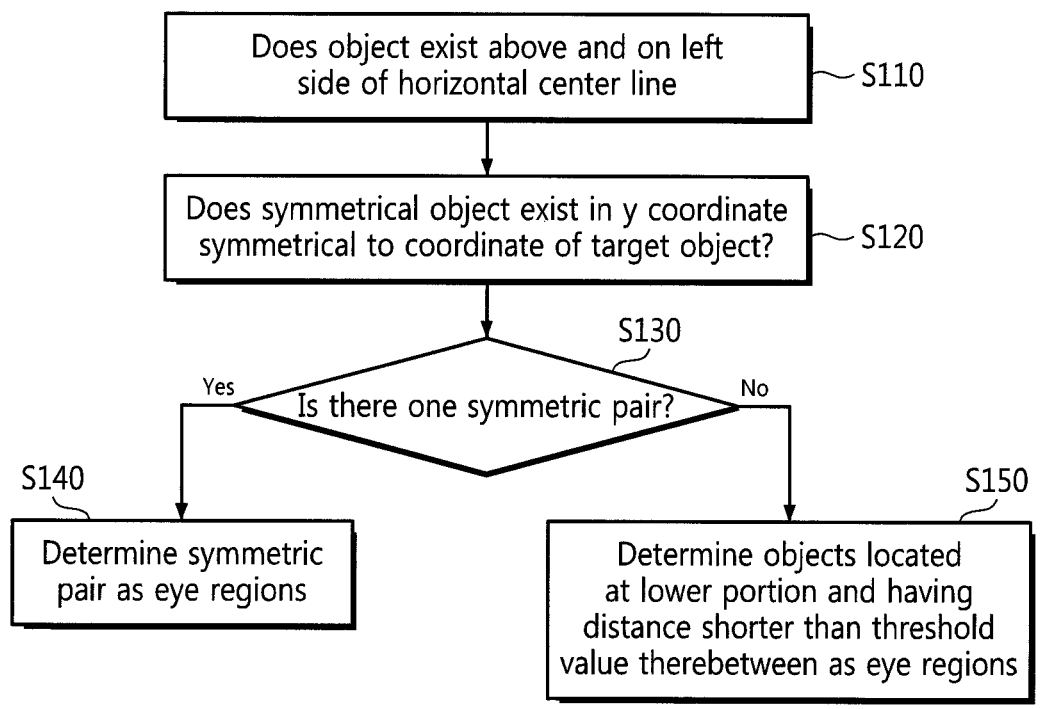
FIG. 13 is a flowchart for detecting eyes in an ocular inspection method according to an embodiment of the present invention.

FIG. 13 is a flowchart for detecting eyes in an ocular inspection method according to an embodiment of the present invention. The ocular inspection method may be performed by the ocular inspection determination engine 332 of the diagnostic data processing system 10 of FIG. 1.

It is examined whether an object exists above and on the left side of the horizontal center line of the face region (step S110), and if an object exists above and on the left side of the horizontal center line of the face region as a result of the examination at step S110, it is examined whether a symmetrical object exists in the y coordinate symmetrical to the coordinate of the target object (step S120), and if a symmetrical object exists in they coordinate as a result of the examination at step S120, it is examined whether there is only one symmetric pair (step S130).

If there is only one symmetric pair as a result of the examination at step S130, the symmetric pair is determined as eye regions (step S140), and if it is determined otherwise at step S130, objects located at a lower portion and having a distance shorter than a threshold value therebetween are determined as eye regions (step S150). The reason is to distinguish the eyes from the eyebrows located above the eyes.

Accordingly, according to change of design, objects located at an upper portion and having a distance shorter than a threshold value therebetween may be determined as eyebrow regions at step S150.

Figure 14:
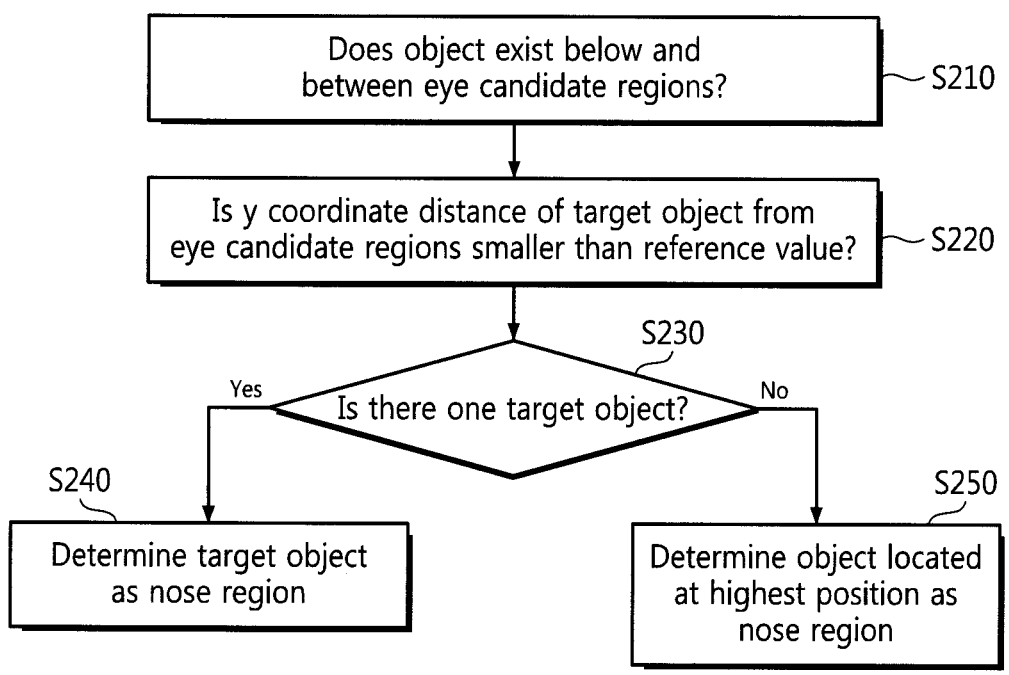
FIG. 14 is a flowchart for detecting a nose in an ocular inspection method according to an embodiment of the present invention.

FIG. 14 is a flowchart for detecting a nose in an ocular inspection method according to an embodiment of the present invention. The ocular inspection method may be performed by the ocular inspection determination engine 332 of the diagnostic data processing system 10 of FIG. 1.

It is examined whether an object is located below and between the eye regions (step S210), and if an object is located below and between the eye regions as a result of the examination at step S210, it is examined whether the y coordinate distance of the target object from the eye regions is smaller than a reference value (step S220), and if the distance is smaller than a reference value as a result of the examination at step S220, it is examined whether there is one target object (step S230).

If there is one target object as a result of the examination at step S230, the target object is determined as a nose region (step S240), and if it is determined otherwise at step S230, an object located at the highest position is determined as a nose region (step S250).

Figure 15:
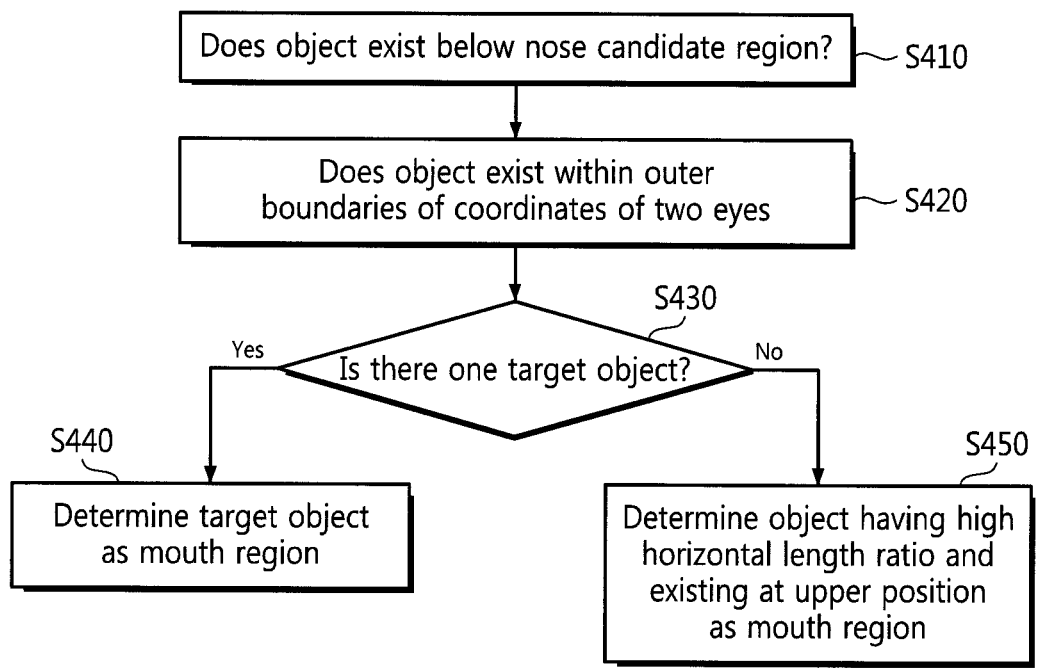
FIG. 15 is a flowchart for detecting a mouth in an ocular inspection method according to an embodiment of the present invention.

FIG. 15 is a flowchart for detecting a mouth in an ocular inspection method according to an embodiment of the present invention. The ocular inspection method may be performed by the ocular inspection determination engine 332 of the diagnostic data processing system 10 of FIG. 1.

It is examined whether an object exists below the nose region (step S410), and if an object exists below the nose region as a result of the examination at step S410, it is examined whether the object exists within outer boundaries of the coordinates of the two eyes (step S420), and if the object exists within the outer boundaries of the coordinates of the two eyes as a result of the examination at step S420, it is examined whether there is one target object (step S430).

If there is one target object as a result of the examination at step S430, the target object is determined as a mouth region (step S440), and if it is determined otherwise at step S430, an object having a high horizontal length ratio and located at an upper portion is determined as a mouth region (step S450).

Figure 16:
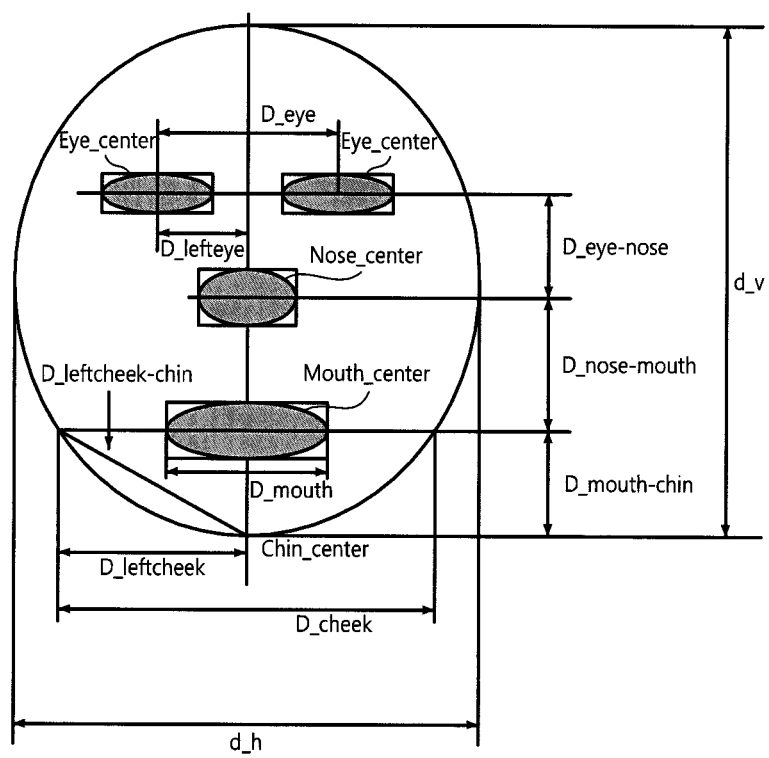
FIGS. 16 and 17 are views for determining correlations between feature points in an ocular inspection method according to an embodiment of the present invention.
Figure 17:
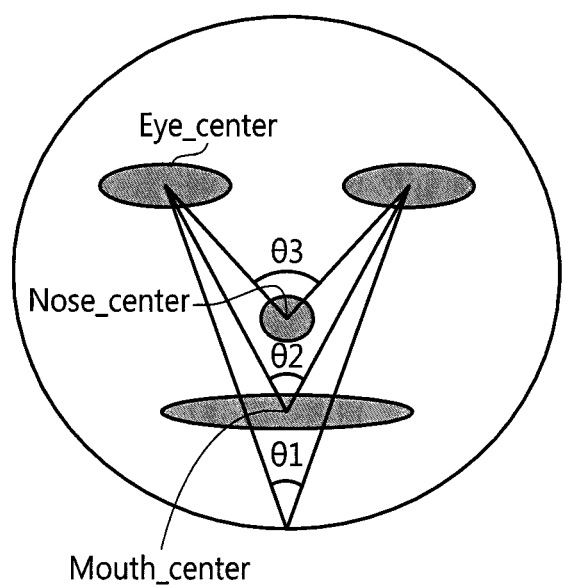

FIGS. 16 and 17 are views for determining correlations between feature points in an ocular inspection method according to an embodiment of the present invention. The ocular inspection method may be performed by the ocular inspection determination engine 332 of the diagnostic data processing system 10 of FIG. 1.

If the face region, the eye regions, the nose region and the mouth region are determined according to FIGS. 12 to 15, the ocular inspection determination engine 332 may analyze correlations between the feature points as shown in FIGS. 16 and 17.

Referring to FIG. 16, the correlations between the feature points include a horizontal distance D_h and a vertical distance D_v of the face region, a distance between the center points Eye_center of the two eyes, a distance D_left-eye between the vertical center line and the left eye, a distances between the center points Eye_center of the two eyes and the center point Nose_center of the nose, a distance between the center point Nose_center of the nose and the center point Mouth_center of the mouth, a distance D_mouth-chin between the center point Mouth_center of the mouse and the center point Chin_center of the chin, a distance D_cheek between the two cheeks corresponding to two points where a horizontal line crossing the center point of the mouth Mouth_center meets the face region, a distance D_leftcheek between the vertical center line and the left cheek, and a distance D_leftcheek-chin between the left cheek and the center point Chin_center of the chin.

Referring to FIG. 17, the ocular inspection determination engine 332 may analyze the correlations between the feature points through an angle created when the center points Eye_center of the two eyes are connected to the center point Nose_center of the nose, an angle created when the center points Eye_center of the two eyes are connected to the center point Mouth_center of the mouth, and an angle created when the center points Eye_center of the two eyes are connected to the center point Chin_center of the chin.

Figure 18:
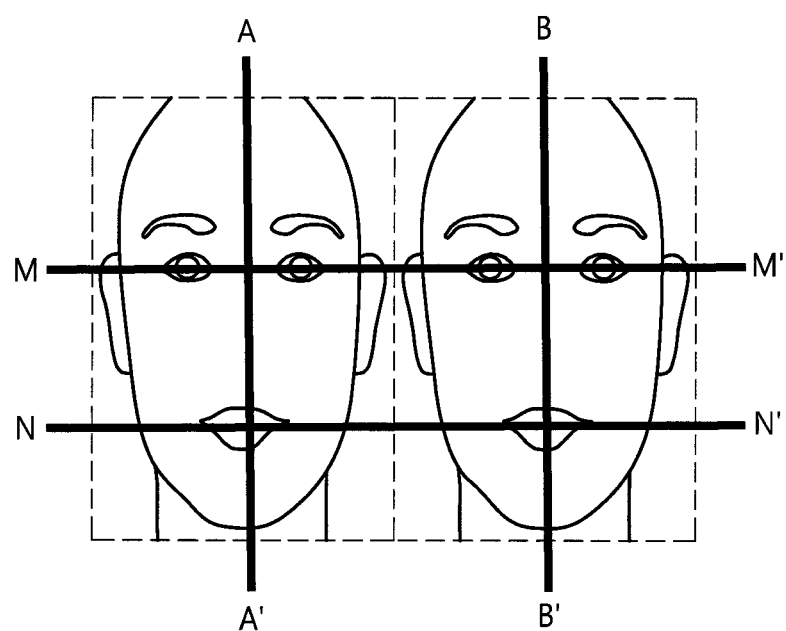
FIGS. 18 to 20 are views for determining a correlation with a backbone through symmetry of a body in an ocular inspection method according to an embodiment of the present invention.
Figure 19:
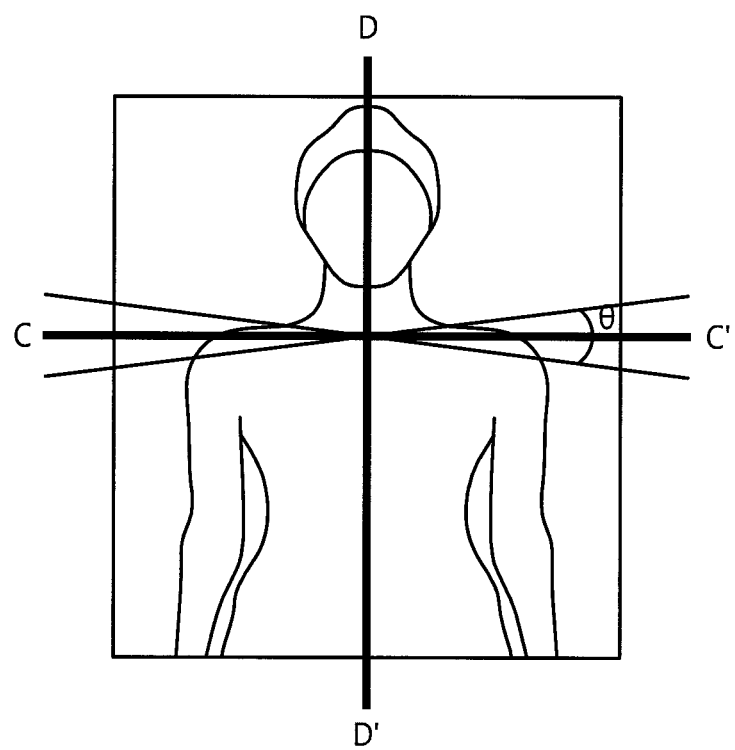
Figure 20:
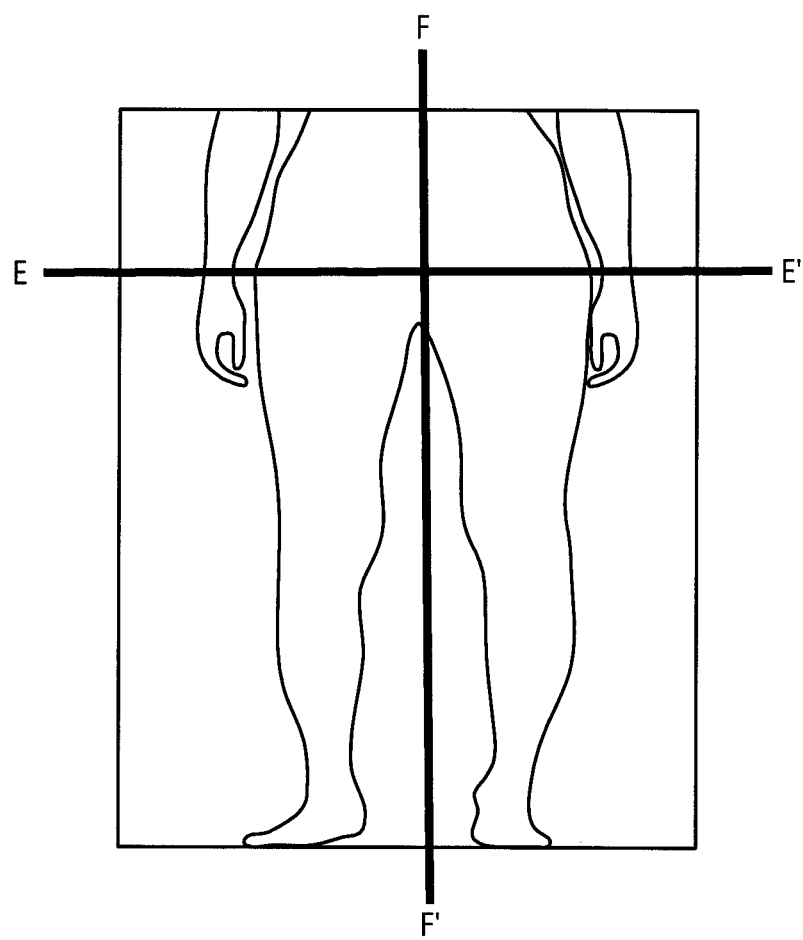

FIGS. 18 to 20 are views for determining a correlation with the backbone through symmetry of a body in an ocular inspection method according to an embodiment of the present invention. The ocular inspection method may be performed by the ocular inspection determination engine 332 of the diagnostic data processing system 10 of FIG. 1.

Referring to FIG. 18, the ocular inspection determination engine 332 determines symmetry of the feature points of the face region to determine an alignment state of the cervical vertebrae.

Referring to FIG. 19, the ocular inspection determination engine 332 extracts the contour of the shoulder line and calculates a horizontally inclined angle of the shoulder line to determine the alignment state of the thoracic vertebrae.

Referring to FIG. 20, the ocular inspection determination engine 332 also determines symmetry of the pelvic region and calculates an inclined angle of the pelvic region to determine the alignment state of the lumbar.

According to the apparatus and system for processing diagnostic data on the basis of medical interview data and camera data according to the present invention, there is an effect of improving health of an individual by processing the diagnostic data on the basis of medical interview data and camera data by utilizing complementary and alternative medicine.

What is claimed is:

1. A diagnostic data processing method comprising:
   pre-storing a group of medical interview questions subdivided into a plurality of subgroups;
   selecting only one representative question from each subgroup, transmitting a first questionnaire including the selected representative questions only to a mobile terminal through a mobile network, and determining a provisional state of a user based on first answers received in response to the representative questions, wherein a total number of the selected representative questions included in the first questionnaire is identical to a total number of the plurality of subgroups;
   transmitting a second questionnaire including all of the group of medial interview questions including the selected representative questions to the mobile terminal through the mobile network when the provisional state of the user is determined as mibyou based on the first answers, determining a final state of the user based on second answers received in response to all the questions in the group, and performing a first diagnosis by analyzing the second answers;
   recognizing a face region from a picture or image received from the mobile terminal, extracting major parts from the face region, and performing a second diagnosis based on the face region and the extracted major parts;
   setting a range of a numeric value of a specific color corresponding to a facial skin color to recognize the face region, setting a region showing numeric value recognized within the range as a face candidate region, and applying an ellipsoidal mask operation to the face candidate region; and
   transmitting proposed complementary and alternative medical contents corresponding to the first and second diagnosis to the mobile terminal.

2. A diagnostic data processing apparatus comprising:
   a processor configured to:
   pre-store a group of medical interview questions subdivided into a plurality of subgroups;
   select only one representative question from each subgroup, transmit a first questionnaire including the selected representative questions only to a mobile terminal through a mobile network, and determine a provisional state of a user based on first answers received in response to the representative questions, wherein a total number of the selected representative questions included in the first questionnaire is identical to a total number of the plurality of subgroups;
   transmit a second questionnaire including all of the group of medial interview questions including the selected representative questions to the mobile terminal through the mobile network when the provisional state of the user is determined as mibyou based on the first answers, determine a final state of the user based on second answers received in response to all the questions in the group, and perform a first diagnosis by analyzing the second answers;
   recognize a face region from a picture or image received from the mobile terminal, extract major parts from the face region, and perform a second diagnosis based on the face region and the extracted major parts;
   set a range of a numeric value of a specific color corresponding to a facial skin color to recognize the face region, set a region showing numeric value recognized within the range as a face candidate region, and apply an ellipsoidal mask operation to the face candidate region; and
   transmit proposed complementary and alternative medical contents corresponding to the first and second diagnosis to the mobile terminal.

3. The apparatus of claim 2, wherein the major parts correspond to feature points of the face region, and the processor detects and formulates locations of the feature points and a ratio of distance between the feature points as an evaluation function and performs a diagnosis on the state of the user through information on the formulated evaluation function.

4. The apparatus of claim 2, wherein if there are two or more set face candidate regions, the processor determines a face region of a largest label as a face region.

5. The apparatus of claim 2, wherein to extract eyes, which is a major part, the processor examines whether a target object exists above and on a left side of a horizontal center line of the face region, examines whether a symmetrical object exists in a y coordinate symmetrical to a coordinate of the target object if the target object exists above and on a left side of a horizontal center line of the face region, and determines a symmetrical pair as eye regions if there is one symmetric pair as a result of the examination.

6. The apparatus of claim 5, wherein to extract a nose, which is a major part, the processor examines whether a target object is located below and between the eye regions, examines whether a y coordinate distance of the target object from the eye regions is smaller than a reference value if the target object is located below and between the eye regions as a result of the examination, and determines the target object as the nose region if there is one target object as a result of the examination.

7. The apparatus of claim 6, wherein to extract a mouth, which is a major part, the processor examines whether a target object exists below the nose region, examines whether the target object exists within outer boundaries of coordinates of the two eyes if the target object exists below the nose region, and determines the target object as the mouth region if there is one target object as a result of the examination.

8. The apparatus of claim 7, wherein if feature points including the face region, the eye regions, the nose regions and the mouth regions are determined, the processor analyzes correlations between the feature points.

9. The apparatus of claim 8, wherein the processor determines a correlation with a backbone through symmetry of a body, including symmetry of the feature points of the face region, angular symmetry of inclined shoulder lines, and symmetry of a pelvic region.

* * * * *